(12) United States Patent
Medina

(10) Patent No.: US 7,412,272 B2
(45) Date of Patent: Aug. 12, 2008

(54) FINGER SLEEVE SENSOR HOLDER

(75) Inventor: Lily Anjanette Medina, Longmont, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 411 days.

(21) Appl. No.: 11/035,083

(22) Filed: Jan. 13, 2005

(65) Prior Publication Data

US 2006/0173247 A1 Aug. 3, 2006

(51) Int. Cl.
*A61B 5/00* (2006.01)

(52) U.S. Cl. ............................................. 600/344

(58) Field of Classification Search ............ 600/340, 600/344, 323

See application file for complete search history.

(56) References Cited

U.S. PATENT DOCUMENTS

| | | | | |
|---|---|---|---|---|
| 4,825,879 A | 5/1989 | Tan et al. | ...................... | 128/633 |
| 4,982,744 A | 1/1991 | Stanec | .......................... | 128/877 |
| 5,090,410 A | 2/1992 | Saper et al. | ................... | 128/633 |
| 5,311,865 A * | 5/1994 | Mayeux | ........................ | 600/340 |
| 5,437,275 A | 8/1995 | Amundsen et al. | ........... | 128/633 |
| 5,511,546 A * | 4/1996 | Hon | .............................. | 600/490 |
| 5,800,349 A | 9/1998 | Isaacson et al. | .............. | 600/323 |
| 5,810,724 A * | 9/1998 | Gronvall | ....................... | 600/323 |
| 5,817,010 A | 10/1998 | Hibl | | |
| 36,000 A | 12/1998 | Swedlow et al. | ............. | 128/633 |
| 5,904,654 A | 5/1999 | Wohltmann et al. | .......... | 600/481 |
| 5,913,819 A | 6/1999 | Taylor et al. | ................. | 600/323 |
| 5,919,133 A | 7/1999 | Taylor et al. | | |
| 5,991,648 A | 11/1999 | Levin | .......................... | 600/344 |
| 6,047,201 A | 4/2000 | Jackson, III | ................. | 600/344 |
| 6,061,584 A | 5/2000 | Lovejoy et al. | .............. | 600/344 |
| 6,256,523 B1 | 7/2001 | Diab et al. | .................... | 600/323 |
| 6,622,034 B1 * | 9/2003 | Gorski et al. | ................ | 600/344 |
| 2005/0075550 A1 * | 4/2005 | Lindekugel | .................. | 600/344 |

* cited by examiner

*Primary Examiner*—Eric F Winakur
*Assistant Examiner*—Estub D Berhanu
(74) *Attorney, Agent, or Firm*—Marsh Fischmann & Breyfogle LLP

(57) ABSTRACT

A conformable medical sensor is provided that has particular applicability for positioning a pulse oximeter sensor relative to a patient appendage. In one embodiment, the sensor holder includes a patient engaging member that is plastically deformable to permit the sensor holder to be conformed to the patient appendage, and plastically deformable to provide a retention force relative to the patient appendage. For example, the engaging member may be bent into a first shape that disposes first and second portions of the sensor holder into an opposing relationship the for receiving a patient appendage therebetween. Once deformed, the engaging member may be elastically deformed to a second shape to provide a retention force so as to maintain the sensor holder and a sensor interconnected thereto in contact with the patient appendage. In another embodiment, and the sensor holder may include a deformable backing layer that is plastically and elastically deformable, as described above, together with a patient interface layer having a recess located for the receipt of the sensor therein.

33 Claims, 7 Drawing Sheets

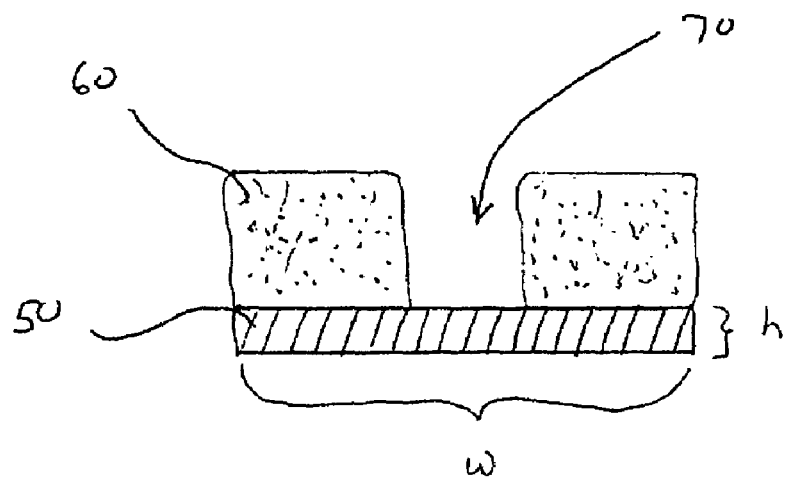
5a
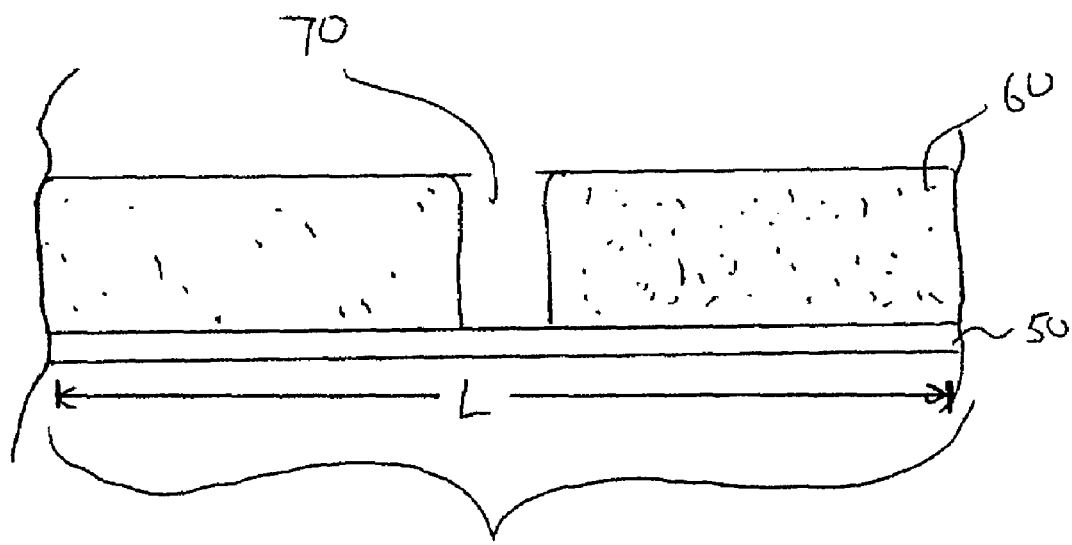
5b

FINGER SLEEVE SENSOR HOLDER

FIELD OF THE INVENTION

The present invention is generally directed to a holder for positioning a medical sensor relative to patient tissue. More specifically, the present invention is directed to a conformable holder for use in securely positioning a medical sensor relative to a patient appendage without requiring the use of adhesives or separate securing devices.

BACKGROUND

In many medical applications it is desirable to hold one or more medical sensors in contact with a patient's tissue such that various non-invasive measurements of physiological parameters may be non-invasively monitored. For example, medical sensors may be held in contact with a patient's tissue to non-invasively determine pulse rates, blood pressure, temperature, and/or blood oxygenation levels. Common to many non-invasive medical sensors is the need to properly position the sensor relative to the patient's tissue to ensure proper sensor operation. For example, if a sensor is held too loosely relative to the tissue it may not function; in contrast, if a sensor is held too tightly to the tissue, the sensor itself may interfere with the physiological parameter(s) it is supposed to monitor.

A common technique used to monitor blood oxygen levels is pulse oximetry, which utilizes light signals transmitted through living tissue to determine light attenuation caused by various blood components. In this regard, pulse oximetry sensors generally include one or more light emitters and detectors that are held in contact with the tissue of a patient. Transmittance type pulse oximetry sensors transmit light through a portion of tissue and detect the non-absorbed light passing through that tissue. In this regard, transmittance type sensors require that the light source(s) and detector(s) be held relative to a patient such that an optical path exists through that tissue between the light emitters and light detectors (e.g., through an appendage such as a finger, ear lobe, hand, foot, etc.). Accordingly, the emitters and detectors of transmittance type pulse oximetry sensors must both be properly positioned relative to the patient tissue to ensure their proper operation. In this regard, a means for securely positioning the pulse oximetry sensor relative to an appendage of a patient is required. It is especially important in positioning the reusable sensor to provide good conformance between the light emitters/detectors and the patient's tissue as well as securing the light source(s) and detector(s) on opposing appendage surfaces to provide an optical path through the tissue between the light sources and detectors. Further, the sensor holding means should be adapted for ready application and removal from the patient with minimal patient discomfort and ease of use for the applicator.

SUMMARY OF THE INVENTION

It is therefore an objective to provide a sensor holder that securely holds a pulse oximetry sensor relative to a patient appendage.

Another objective is to provide a sensor holder that requires no fasteners to securely hold a pulse oximetry sensor relative to a patient appendage.

These and additional objectives are achieved by the present invention which provides a sensor holder for use in positioning a medical sensor relative to a patient appendage. The sensor holder is particularly apt for use in positioning pulse oximetry sensors relative to a patient appendage such that an optical path is created through that appendage between a light emitter and light detector. However, it will be appreciated that the sensor holder disclosed herein may be utilized with other non-invasive medical sensors as well. That is, any sensors that are held in contact with the tissue of a patient.

In a first aspect of the invention, a sensor holder is provided that contains a patient engaging member that is plastically deformable to allow the sensor holder to be conformed about an appendage of a patient, such as a finger, as well as elastically deformable to provide a retention force. That is, the deformable engaging member may be bent into a first shape to, for example, dispose first and second portions of the sensor holder in an opposing relationship (e.g. U-shaped to engage opposing surfaces of a patient appendage).

Once deformed into a desired shape, the plastically deformable member may be elastically deformed to a second shape to provide a retaining force, in the manner of a paper clip, to maintain the sensor holder and a sensor interconnected thereto in contact with a patient appendage. For example, the opposing surfaces of a U-shaped member may be slightly sprung to allow the firm insertion of a patient appendage therebetween. By utilizing the plastically deformable member, the sensor holder of the present invention may be shaped to conform to a variety of patient appendages while providing a customizable fit for that appendage. Furthermore, by utilizing elastic deformation of the shaped member to provide retention force, the sensor holder may be applied to an appendage without the use of adhesives or other connectors. However, an adhesive material may additionally be provided on a patient contact surface to further enhance the retention/holding force of the sensor holder.

A medical sensor may be interconnected to the deformable engaging member in any manner so long as the sensor is held in a conformal relation with a patient's tissue upon application of the sensor holder to the appendage. For example, the sensor holder may receive a sensor in a recess, a pocket, or other attachment device for holding the existing sensor relative to the sensor holder. Alternatively, the engaging member may be incorporated into a medical sensor. That is, one or more sensor components (e.g. a light emitter and/or detector for a pulse oximetry sensor) may be permanently mounted directly to the engaging member. As a further alternative, the sensor may be held by friction or pressure. That is, the sensor, along with a patient's appendage, may be compressed between opposing surfaces of the patient engaging member.

Additions and various refinements of the noted features exist, these refinements and additional features may be provided separately or in any combination. For example, the engaging member may be formed of any material that imparts the desired mechanical characteristics to the sensor holder. As used herein, the term "plastically deformable" refers to deformation of a body caused by an applied stress, wherein the deformation remains after the stress is removed. The term "elastically deformable" refers to the deformation of a body caused by an applied stress, wherein the body returns to its original shape after the stress is removed. For any material, an elastic limit (also known as yield strength) is the separation point between elastic and plastic deformation characteristics. That is, an applied stress beneath the elastic limit results in elastic deformation, whereas an applied stress above the elastic limit results in plastic deformation (or breakage for brittle materials). In any case, the selected material should have an elastic limit that allows the engaging member to be manipulated (i.e., plastically deformed) by hand from a first shape to a second shape while providing adequate elastic deformation characteristics to allow the engaging member to act as a spring to hold the sensor holder on the patient appendage.

As will be appreciated, the elastic limit or total yield strength of a member is generally dependant on one or more physical and material factors. These factors include the moment of inertia about the axis which a stress is applied (i.e. which is dependant upon the physical dimensions of that material) as well as the modulus of elasticity for that material. In any case, by varying the dimensions (e.g., cross-sectional size and/or length) of the engaging member as well as the material used to form the engaging member, any of a variety of materials may provide the desired deformation properties. A non-inclusive list of materials includes isotropic materials such as aluminum, plastics, and rubbers, as well as composite materials such as metallic wires immersed in a rubberized matrix, etc. What is important is that the material utilized provides the desired plastic deformation to enable first and second portions of the sensor holder to be disposed on opposing surfaces of an appendage as well as the desired elastic deformation to act as a spring to provide a restraining force once applied to an appendage.

As noted, upon application to a patient appendage, the sensor holder may generally comprise a U-shape in which first and second portions of the engaging member may be disposed on opposing surfaces of that appendage. In this regard, it will be appreciated that if the opposing surfaces of the engaging member are spaced at a distance slightly less than the outside diameter of the appendage, these first and second opposing portions may be sprung (i.e. elastically deformed) relative to one another to allow the appendage to be inserted therebetween. This elastic deformation provides a resilient restoring force that is utilized to apply a compressive force to the appendage and maintain the sensor holder in contact with the appendage. The plastic/elastic sensor holder is particularly apt for applying pulse oximetry sensors to patient appendages. That is, the sensor holder is able to secure a pulse oximetry sensor in contact with a patient appendage and, preferably apply a retention/holding force that is sufficient to maintain the sensor in contact with the patient tissue. In this regard, the size (e.g., cross-sectional, length, etc) of the sensor holder may be adjusted at manufacture to establish a desired holding force. As will be appreciated for specialized applications, such as premature infants, the sensor holder may be designed to apply a lower holding force.

A second aspect of the present invention provides a sensor holder that includes: a deformable backing layer that is plastically deformable from a first configuration to a second configuration; a patient interface layer having a first surface interconnected to the deformable backing layer and a second inside surface for interfacing with a patient appendage; and a sensor recess located on the inside surface of the patient interface layer for selectively receiving a sensor. Prior to application to a patient appendage, the sensor holder may be in any first configuration (e.g., planer, an open U-shape, etc) that allows a patient appendage to be disposed relative to the inside surface of the patient interface layer. In order to be applied to a patient appendage, the deformable backing layer of the sensor holder may then be plastically deformed (i.e., bent) into a second configuration to engage opposing surfaces of a patient appendage. In this regard, the sensor holder may be custom-sized for an appendage. For example, the sensor holder may be bent into a U-shape such that at least a first and second portion of the sensor holder are in an opposing relationship and contacting opposing surfaces of an appendage. As will be appreciated, the appendage may be removed to allow an additional plastic deformation of the deformable backing layer. Upon insertion of the appendage, the opposing surfaces may elastically deform relative to one another allowing those surfaces to apply a compressive retaining force to the patient appendage. If desired, the patient interface layer may further include an adhesive (e.g., covered by a removable release liner). Such an adhesive may be utilized to increase the retention force of the sensor in high patient movement conditions.

The patient interface layer may be formed of any appropriate material. However, in one embodiment the patient interface layer is formed of a compressible material to provide cushioning between the sensor holder and the appendage of the patient. In this regard, the compressible material may have a compression setting that, upon application of a predetermined pressure to the material, substantially conforms to the surface contacting the compressible material (e.g., a patient's finger). In this regard, the compressible material may have a plurality of void spaces to permit compression. Preferred compressible material is open or closed cell foam, neoprene, rubber, fabric, and composites thereof, with foam being the most preferred. As will be appreciated, use of a compressible material for the patient interface also allows for better sensor holder to appendage conformance, which may provide for improved retaining forces between the sensor holder and to the appendage.

The recess located on the inside surface of the sensor holder may be configured to matingly receive a correspondingly-shaped sensor. For example, some pulse oximetry sensors are in an L-shaped or T-shaped configuration having light emitters and light detectors that are somewhat spaced relative to one another. Generally, these spaced sensors are utilized for transmitting radiation through a tissue path by disposing the emitters and detectors on opposing surfaces of a patient appendage. Accordingly, the recess may be configured to matingly receive these sensors. That is, the sensor recess may have a first portion for receiving the light emitter(s) and a second portion for receiving the light detector(s).

In one embodiment, the first part of the sensor recess will be located on the first portion of the sensor holder and a second part of the sensor recess will be located on a second portion of the sensor holder. In this embodiment, when the backing layer is plastically deformed and the first and second portions of the sensor holder are in an opposing relationship, the first and second parts of the sensor recess will also be in an opposing relationship. As will be appreciated, this allows for a pulse oximetry sensor having a light emitter and light detector located in the first and second parts of the sensor recesses to be disposed on opposing surfaces of a patient appendage upon application of the sensor holder to that appendage.

The recess will generally have a depth that allows the inside surface of the patient interface layer (i.e., the interface surface) and a top surface of the sensor to be substantially planer upon application to a patient appendage. As will be appreciated, this prevents any pressure points being applied to the patient's tissue by the sensor while maintaining a conformal relationship between the light emitter/detector and the patient's tissue. Finally, the sensor recess may contain some sort of retainer to hold the sensor within the recess. This retainer may be any mechanism that secures the sensor within the recess prior to application to the appendage. Non-limiting examples of retainers include adhesives, hook and loop connectors, pockets formed within the patient interface layer to receive the sensor, and slits through the backing layer through which the sensor may be threaded. In one embodiment, the retainer is an adhesive coating on the bottom of the recess covered by a peel-away release sheet.

According to a third aspect of the present invention, a sensor holder is provided for holding a sensor relative to a patient appendage. The sensor holder of the third aspect includes a first member for engaging a first portion of a patient appendage, a second member for engaging a second portion of a patient appendage, and a plastically deformable interconnecting member that interconnects the first member to the second member, wherein at least one of the first and second members for selectively interconnectable to a sensor. The plastically deformable interconnecting member allows selective positioning of the first member relative to the second member and thereby facilitates application of the sensor holder to a wide variety of appendages. Additionally, the plastically deformable interconnecting member is elastically deformable to provide a spring-like retention force to maintain the sensor holder relative to a patient appendage.

Additions and various refinements of the noted features exist, these refinements and additional features may be provided separately or in any combination. For example, the first and second members may each comprise a rigid member (in comparison with the interconnecting member) for interfacing opposing surfaces of a patient appendage. Furthermore, these first and second members may be shaped to conformably engage a patient appendage. For example, in the case of a sensor holder for use in engaging a finger, the first and second members may be semi-cylindrical along the axis of finger insertion. Furthermore, these first and second members may further include a compressible material layer for added patient comfort as well as providing convenient surface for interconnecting a sensor.

The plastically interconnecting deformable member, as in the above-described aspect, may be any material that imparts the desired mechanical properties. However, in the subject aspect, the plastically deformable member may be made of a material different than the material(s) utilized to form the first and second members. For instance, the first and second members may be formed from a rigid plastic material while the interconnecting material is formed from a soft/ductile metal. This interconnecting member may be interconnected to the first and second members in any appropriate manner including, but not limited to, overmolding, adhesion, and/or using physical connectors (e.g., rivets, screws, etc.)

According to a fourth aspect of the present invention, a method for positioning a sensor relative to a patient appendage is provided. The method includes the steps of providing a plastically deformable sensor holder that includes at least one sensor recess on a patient interface surface; locating a sensor in the recess; locating a patient appendage relative to a first portion of the sensor holder; and applying a force to the sensor holder in order to dispose a second portion of the sensor holder in an opposing relationship with the first portion of the sensor holder, wherein the appendage is disposed between the opposing first and second portions. The step of providing may entail providing a sensor holder specifically designed for use with a particular patient appendage.

The first locating step of the method generally includes seating a sensor into a sensor recess, which is preferably shaped correspondingly with the sensor. In the case of a pulse oximetry sensor, the step may further entail seating first and second portions of the sensor into first and second portions of the sensor recess. That is, a light emitter portion of the sensor may be seated in a first portion of the recess and a light detector may be seated in a second portion of the recess. As will be appreciated, these recess portions will generally be somewhat spaced to allow the light emitter and light detector to be disposed in an opposing relationship upon application of the sensor to a patient appendage. In this regard, an optical path may be created through the appendage between the light emitter and light detector portions of the sensor.

The step of locating a patient appendage relative to a first portion of the sensor holder will generally be dependent on the configuration of the sensor holder as well as which appendage is to be monitored. In the case of a digit, such as a finger, the digit may be placed over a first portion of the sensor holder, and more preferably, over a first portion of the sensor recess and a sensor contained therein. For example, where a pulse oximeter sensor is utilized, the digit may be placed over the emitter or detector. As will be appreciated, by locating the digit over a portion of the sensor, the sensor may be held in place during manipulation of the sensor holder.

Applying a force to the sensor holder may include applying a bending force to conform the sensor holder about the patient appendage in order to dispose the first and second portions of the sensor holder in an opposing relationship. However, if the sensor holder is already pre-formed to have opposing portions (e.g., U-shaped) the step of applying a force may entail applying a compressive force to the already opposing portions such that they contact opposing surface of an appendage. In any case, when the appendage is disposed between the opposing surfaces of the sensor holder, a compressive force may be applied to the sensor holder such that the sensor holder applies a compressive force to the appendage. As will be appreciated, this compressive force provides a retaining force to maintain the sensor holder on the appendage as well as forcing the surface of the included sensor into contact with the patient appendage.

According to another aspect of the present invention, a method is provided for positioning a medical sensor relative to a patient appendage. The method includes the steps of interconnecting a medical sensor to an appendage-engaging member, plastically deforming the appendage-engaging member to a first shape where first and second portions of the engaging member are disposed in a spaced-opposing relationship (e.g., U-shaped). Once deformed to the first shape, the opposing portions of the engaging member may be elastically deformed to a second shape. As will be appreciated, the elastic deformation causes a resilient restoring force between the first and second portions of the appendage-engaging member. While elastically deformed (i.e. in the second shape), a patient appendage is inserted between the first and second portions of the engaging member whereupon the resilient restoring force is utilized to apply a compressive force to the appendage. That is, force utilized to elastically deform the engaging member is released and the first and second portions of the engaging member attempt to move back to the non-elastically deformed position (i.e. first shape) and thereby clamp onto the patient appendage.

Additional aspects and advantages of the present invention will become apparent to those skilled in the art upon consideration of the further description provided herein below.

BRIEF DESCRIPTION OF THE DRAWINGS

FIGS. 5a and 5b show cross-sectional views of the sensor holder of FIG. 1.

DETAILED DESCRIPTION

Several embodiments of the plastically and elastically deformable sensor holder will now be described in relation to the accompanying drawing which at least assist in illustrating its various pertinent features. For example, FIGS. 1-5b show a first embodiment of a sensor holder that is utilized to hold a generally T-shaped pulse oximetry sensor relative to a finger while FIGS. 6 and 7 show a second embodiment of a sensor holder for use in holding an L-shaped pulse oximetry sensor relative to an earlobe. However, it is to be expressly understood that other embodiments of the sensor holder may be utilized to accommodate different sensors and/or other patient appendages, such as nasal septums, toes, etc. Furthermore, as used herein the term "plastically deformable" is understood to represent permanent deformation of a body in any direction without rupture. That is, the plastically deformable material is able to deform permanently under the application of a stress and maintain that deformation after the stress is removed. The term "elastically deformable" represents the deformation of a body by an applied stress, wherein the body returns to its original shape after the stress is removed. The terms "elastic limit" and "yield strength" interchangeably represent the defining line between elastic deformation and plastic deformation for a material.

Figure 1:
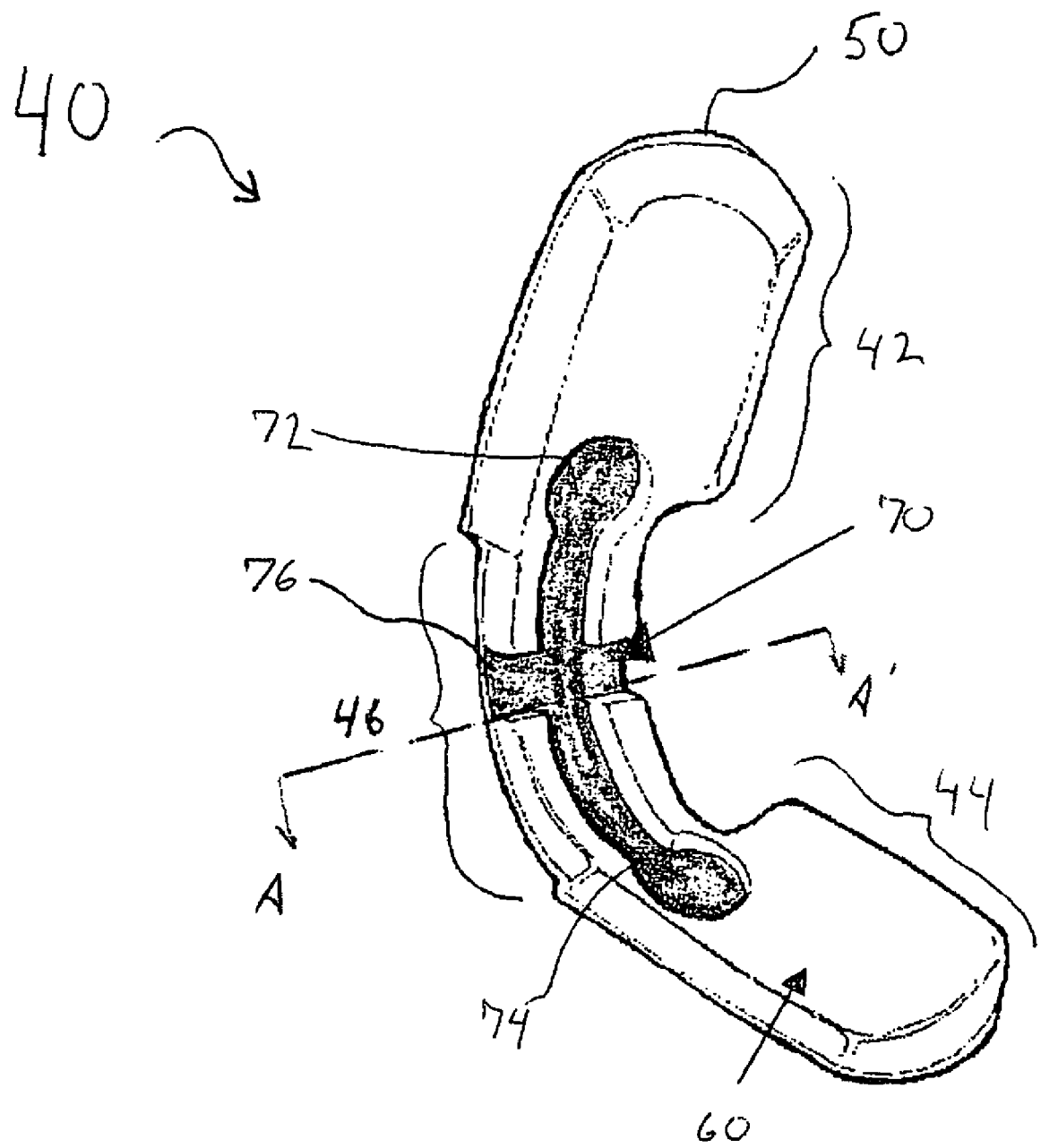
FIG. 1 shows a perspective view of a first embodiment of the plastically deformable sensor holder.

FIG. 1 shows a first embodiment of the sensor holder 40. The sensor holder 40 contains a deformable backing layer 50 that makes up the outside surface or "shell" of the sensor holder 40. In accordance with the present invention, the deformable backing layer is both plastically deformable to allow the sensor holder to maintain a desired shape and elastically deformable to provide a resilient spring-like holding force, as will be more fully discussed herein. Interconnected to the inside surface of the deformable backing layer 50 is a patient interface layer 60 for providing a gentle interface with a patient appendage. The inside (i.e., patient side) surface of the patient interface layer 60 contains a sensor recess 70 that is utilized to selectively receive a sensor and hold the sensor relative to the sensor holder. As shown in FIG. 1, the sensor holder 40 is formed substantially as an elongate member that is particularly apt for application to a finger (see FIG. 4). Referring again to FIG. 1, it is noted that the sensor holder 40 has a semi-arcuate shape prior to application to the finger, however, it will be appreciated that prior to deformation to a desired shape, the sensor holder 40 may have any configuration (e.g. a flat elongated strip).

Figure 4:
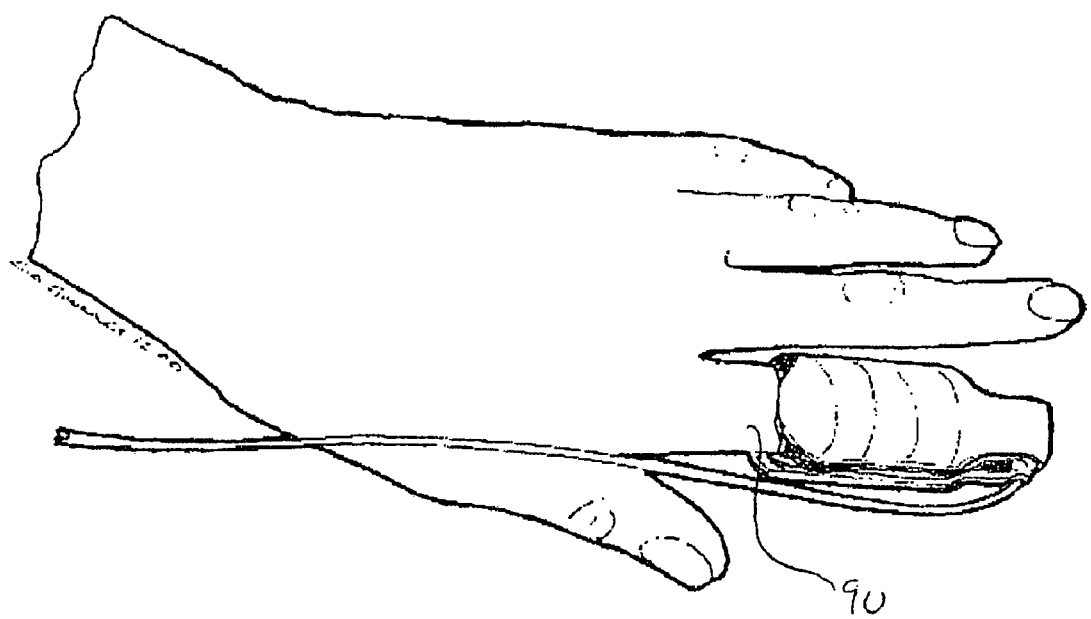
FIG. 4 shows the sensor holder and sensor of FIG. 3 applied to a finger.

Referring to FIG. 1, it will be noted that in this embodiment the sensor holder 40 is generally defined by first and second and portions 42, 44 and a central portion 46 interconnecting the first and second portions 42, 44. Upon application of the sensor holder 40 to the finger, each end portion 42, 44 will be disposed on opposing surfaces of that finger (see FIG. 4). Accordingly, the central portion 46 of the sensor holder 40 plastically deforms to allow the first and second end portions 42, 44 to be disposed in an opposing relationship. That is, the sensor holder 40 is bent to a generally U-shaped configuration. As shown in FIG. 4, when the sensor holder 40 is in the U-shaped configuration, the index finger 90 of a patient is disposed between the first and second end portions 42, 44 as well as being disposed between first and second halves 72, 74 of the sensor recess 70, as will be more fully discussed herein. In this present embodiment, the end portions 42, 44 are each semi-cylindrical in shape to better conform to the finger as well as provide enhanced ambient light-blocking characteristics.

The deformable backing layer 50 may be formed of any material that imparts the desired elastic and plastic deformation properties. That is, the material should have an elastic limit or yield strength that allows a medical technician to easily plastically deform the backing layer 50 to a first shape to engage a patient appendage such as a finger 90. That is, first and second portions 42, 44 of the sensor holder 40 may be easily bent into an opposing relationship to allow these portions to engage opposing surfaces of a patient appendage (see FIG. 4). Furthermore, the deformable material should have an elastic limit that, once conformed to a patient appendage (i.e. plastically deformed to a desired shape), provides enough elastic deformation to create a resilient spring-like retaining force to hold the sensor holder 40 on the appendage. That is, the central portion 46 may be elastically deformed to allow the first and second end portions 42, 44 to slightly spread to allow the finger 90 to be inserted therebetween. Once inserted, the resilient retaining force may compress the finger 90 between the first and second end portions 42, 44.

In order to plastically deform the central section of the sensor holder 40, the yield strength of the backing layer 50 must be overcome. The overall yield strength of an object will depend on the bending moment of inertia of that object as well as the modules of elasticity (E) for the material used to form that object. Referring to FIG. 5a, a cross section of the sensor 40 taken along section lines A-A (not to scale) shows the plastically deformable backing layer 50, the patient interface layer 60 and a portion of the sensor recess 70. As shown, the backing layer 50 is an isotropic layer having a height (h) and a width (w). The moment of inertia (I) for this rectangular cross section is $I=wh^3/12$ where "h" is the height of the rectangle perpendicular to the bending axis and "w" is the width of the rectangle parallel with the bending axis. This moment of inertia can be thought of as the stiffness of the backing layer 50 (e.g., a backing layer with a greater thickness "h" will be stiffer).

As noted, the plastic deformation of the sensor holder 40 of FIG. 1 is generally isolated to the central section 46. In order to plastically deform this section 46, the stress applied (i.e. bending force) must exceed the allowable bending stress (i.e. yield strength) for this section 46, which can be thought of as a beam (see FIG. 5B). It will be appreciated that by increasing the length of the central section, the required bending force will be reduced. In this regard, it will be appreciated by varying the physical parameters (h, w, and/or length) of the bending section (i.e. central section 46) and/or the material utilized for the deformable backing layer 50 (e.g., the modulus of elasticity E), numerous materials may be utilized to provide a deformable backing layer 50 having a predetermined yield strength. As shown, an isotropic plastic material is utilized as the plastically deformable backing layer 50. Additionally, the plastic is opaque to provide added light blocking characteristics for the sensor holder 40. The plastic may have any elastic limit that permits the sensor to easily bend while providing sufficient elasticity to provide an adequate holding force. Other materials that can be utilized include: metals and/or composite materials such as wires encased in a rubberized matrix material.

Generally, the patient interface layer 60 will be formed of a compressible material to provide cushioning between the sensor holder 40 and the appendage of the patient. Further, an adhesive could be incorporated onto the patient interface layer 60 as well (not shown). The compressible material has a compression setting that, upon application of a predetermined pressure, substantially conforms to the surface contacting the compressible material (e.g., a patient's finger). That is, the compressible material preferably has a plurality of void spaces to permit compression. Preferred compressible material is open or closed cell foam, neoprene, rubber, fabric, and composites thereof, with foam being the most preferred.

Figure 2:
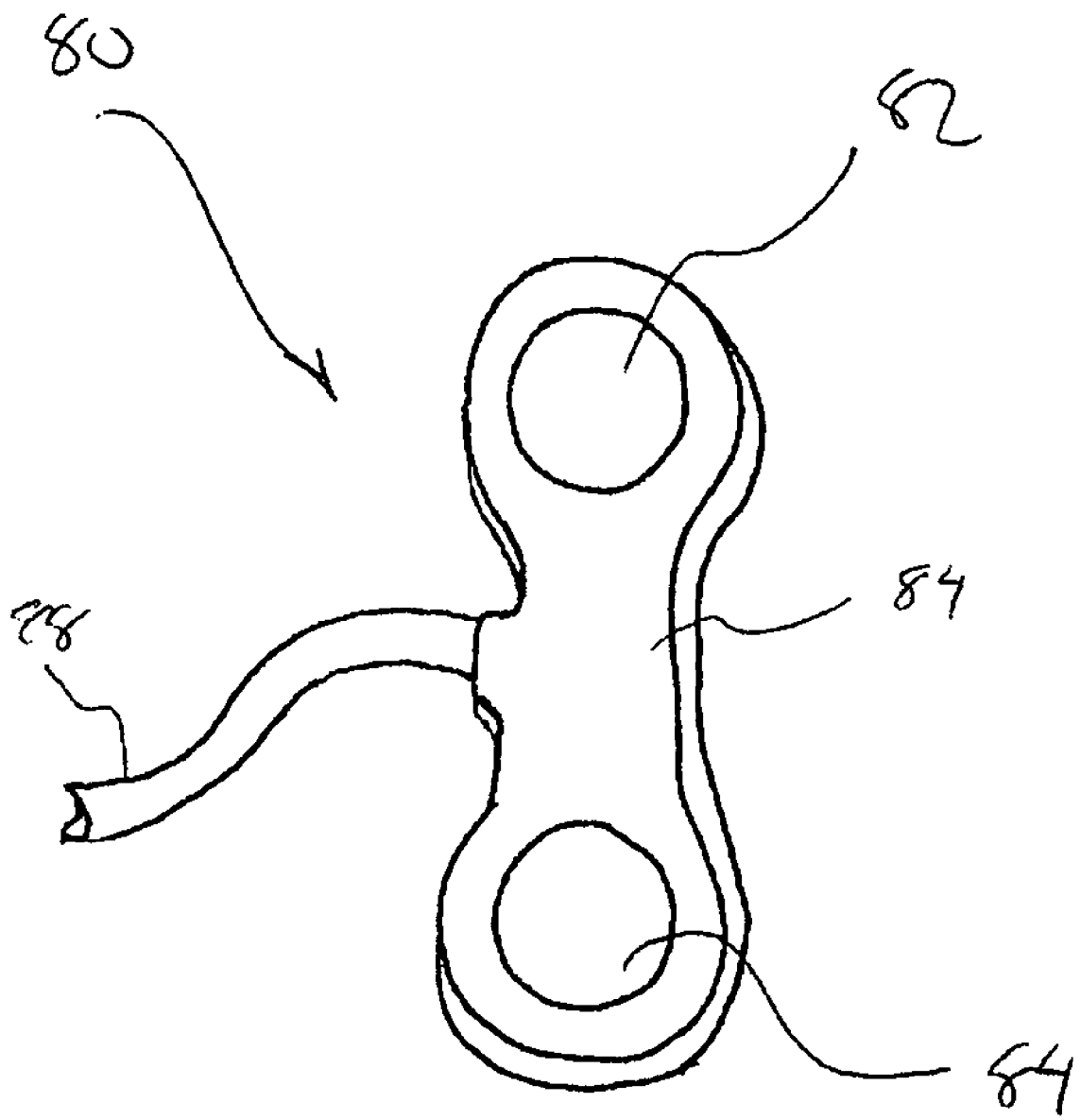
FIG. 2 shows a perspective view of a transmittance type pulse oximeter sensor that may be utilized with the sensor holder of FIG. 1.

FIG. 2 shows a transmittance type pulse oximetry sensor 80 that may be utilized with the sensor holder 40 as shown in FIG. 1. In this regard, the pulse oximetry sensor 80 contains a generally T-shaped configuration, corresponding to the T-shaped configuration of the sensor recess 70 of the sensor holder 40. The pulse oximetry sensor 80 contains an emitting surface 82 that may contain one or more LEDs, as well as a detecting surface 84 that may contain one or more photodiodes. The emitting surface and detecting surface 84 are separated by a flexible conduit portion 84 of the sensor 80 that allows the light emitting surface 82 and light detecting surface 84 to be disposed on opposing surfaces of a patient appendage when the sensor 80 is utilized. Finally, the sensor 80 contains a cable 88 that interconnects the light emitting surface 82 and light detecting surface 84 to appropriately configured monitoring equipment. As will be appreciated, when the transmittance-type pulse oximeter 80 is placed within the recess 70 at least a portion of the finger will be disposed between the light emitting surface 82, and light detecting surface 84 of the sensor 80 such that an optical path is created through the finger.

As noted, the sensor holder 40 contains a recess 70 for use in selectively receiving a sensor. This recess 70 is substantially the same size and shape of the sensor that will be utilized with the sensor holder 40. As shown, the sensor recess 70 is generally T-shaped for use with the T-shaped sensor shown in FIG. 2. Further, the depth of the recess 70 is such that upon application to a patient appendage, the front surface of a sensor 80 contained within the recess 70 will be substantially level with the front surface of the patient interface layer 60. In this regard, the light emitting 82 and light detecting 84 surfaces of the sensor 80 may be held in conformal relationship to the finger without applying pressure thereto. This recess 70 is generally formed by removing a portion of the compressible material utilizing, for example, a cutting dye with the same size and shape as the sensor. That is, the patient interface layer 60 (i.e., a compressible material layer) will have the same thickness as the sensor 80, thereby allowing facilitated formation of the recess 70.

As shown in FIGS. 1 and 2, the recess 70 contains a first half 72 and a second half 74 that are sized and shaped to receive the first and second portions of the sensor 80. That is, the light emitting surface 82 and light detecting surface 84. Furthermore, the recess 70 contains a lateral portion that extends to the lateral edges of the sensor holder 40. This lateral portion 76 of the recess 70 provides an access for the sensor cable 88 from beneath the sensor holder 40 when applied to a finger. That is, the cable 88 of the sensor 80 is routed out one side of the lateral recess portion 76 when the sensor holder 40 is applied to the finger. In this regard, the sensor cable 88 is able to exit the sensor holder 40 without applying pressure to the patient's tissue which may affect sensor readings.

Figure 3:
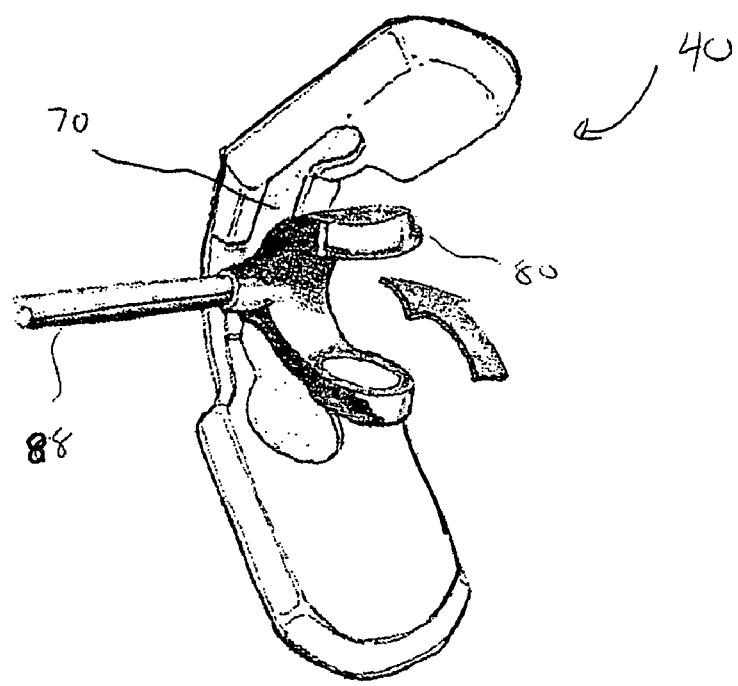
FIG. 3 shows the integration of the sensor of FIG. 2 into the sensor holder of FIG. 1.

FIGS. 3 and 4 show application of the sensor holder 40 to a patient appendage (in this case, the patient's index finger). Initially, a transmittance type pulse oximetry sensor 80 is seated within the sensor recess 70 of the sensor holder 40. As shown in FIG. 3, the plastically deformable backing layer 50 of the sensor holder 40 may be initially deformed such that the sensor holder 40 has an open U-shape. This may entail plastically deforming the central portion 46 of the sensor holder by, for example, grasping the first and second end portions 42, 44 in each hand and bending the central portion 46 to the desired shape. Preferably, the central portion 46 is bent to allow the first and second end portions 42, 44 to be disposed apart a space slightly less than the outside surface of the appendage to which the sensor holder is applied. The tensile force is then applied between the first and second end portions 42, 44 to elastically deform (spring) the central portion 46 as well as slightly spread the first and second end portions 42, 44. The appendage is then inserted into the sensor holder 40. Preferably, the finger is inserted within the sensor holder until it is disposed between the first and second halves 72, 74 of the sensor recess and thereby the emitting surface 82 and detecting surface 84 of the pulse oximetry sensor 80. At this point, the tensile force is released allowing the first and second end portions 42, 44 of the sensor holder with the top and bottom surfaces of the finger 90. As will be appreciated, this compressive force provides a retaining force to maintain the sensor holder 40 relative to the finger 90.

Once the first and second end portions are contacting opposing surfaces of the finger 90, an additional compressive force may be applied to the end portions and central portion 46 to compress the compressible patient interface layer 60 and provide a secure attachment of the sensor holder 40 to the finger. As will be appreciated, this additional compressive force may further plastically deform the backing layer 50 (i.e., crimps the central portion 46) which then acts as a spring that resists opening. In any case, it will be appreciated that by utilizing an elastically and plastically deformable backing layer 50, the sensor holder 40 is able to be applied to the finger without the use of adhesives or other fastening means. This provides a sensor holder that has a reduced part count, is easily manufactured, and is easy for a medical technician to apply and remove.

Figure 6B:
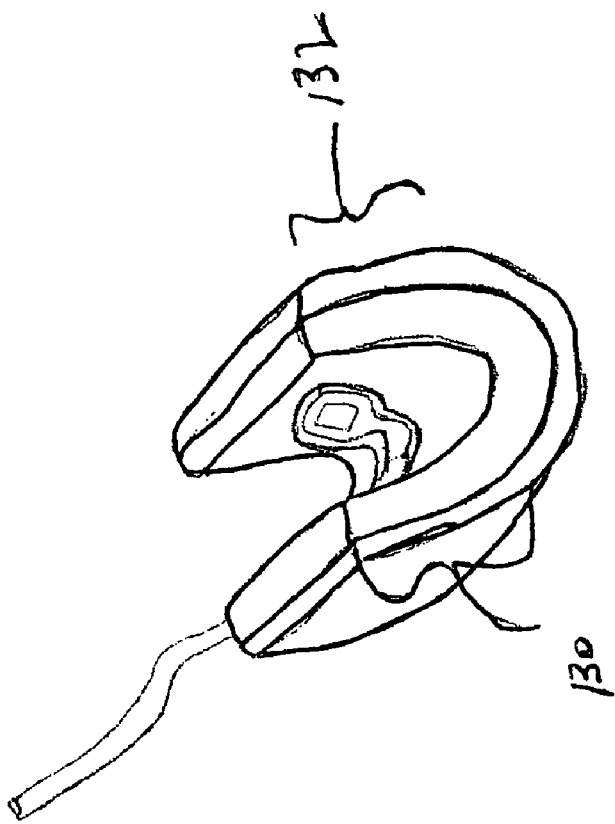
FIGS. 6a and 6b show a second embodiment of the plastically deformable sensor holder.
Figure 6A:
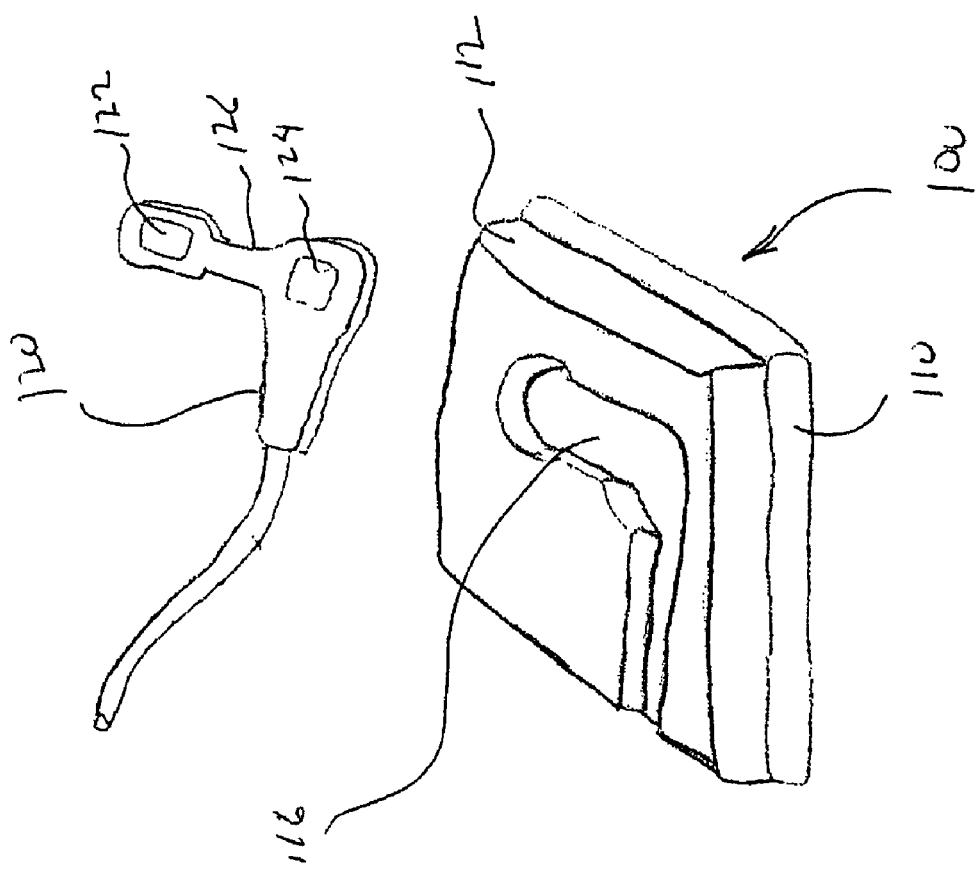
Figure 7:
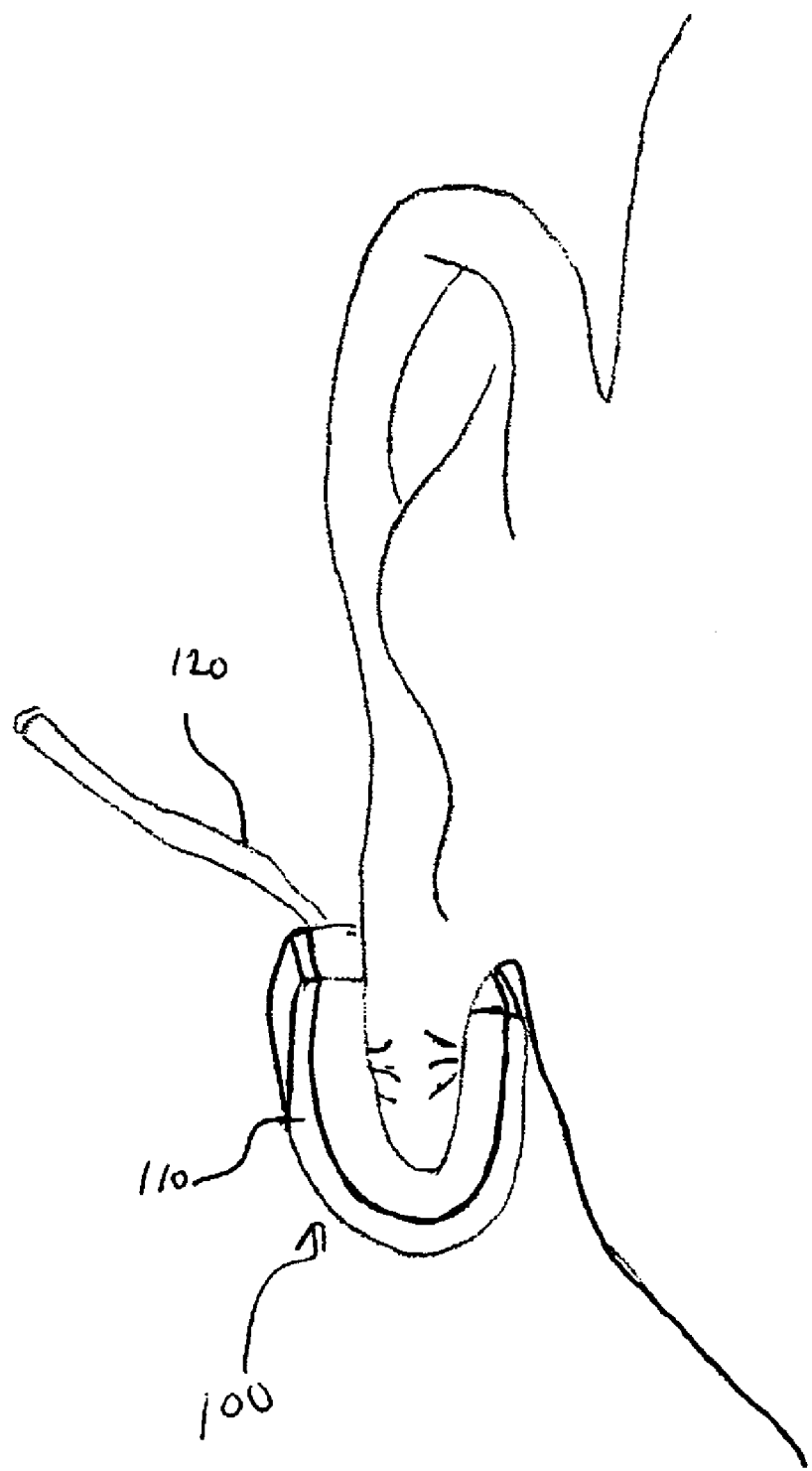
FIG. 7 shows the sensor holder of FIG. 6a and 6b applied to an earlobe.

FIGS. 6*a* and 6*b* show a second embodiment of a plastically deformable sensor holder 100. As in the first embodiment, the second embodiment of the sensor holder 100 contains a deformable backing layer 110 having elastic and plastic characteristics and a compressible patient interface layer 112. These two layers 110, 112 may be formed using material as described above. Formed into the patient side surface of the patient interface layer 112 is an L-shaped recess 116 for selectively receiving an L-shaped sensor 120. Again, this sensor contains a light emitter 122 and a light detector 124. As shown in FIG. 5*b*, the L-shaped sensor 120 is seated within the L-shaped recess 116 and the deformable backing layer is deformed to dispose first and second portions of the sensor holder 100 in an opposing relationship for receiving a patient appendage. Accordingly, the flexible conduit 126 interconnecting the light emitter 122 and light detector 124 of the L-shaped sensor 120 bends to dispose the emitter 122 and the detector 124 in an opposing relationship. FIG. 7 shows the second embodiment of the sensor holder 100 as applied to an earlobe. After insertion of the patient appendage, the deformable backing layer 110 may be crimped to provide a retention force that holds the sensor holder 100 and sensor 120 on the earlobe.

Figure 8:
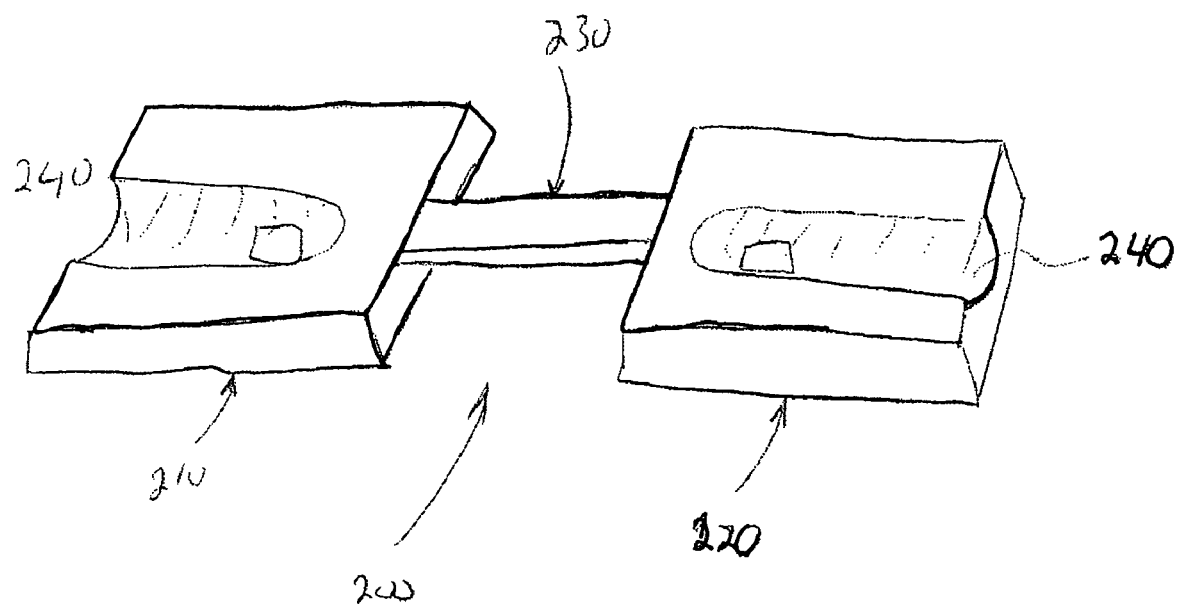
FIG. 8 shows a third embodiment of the plastically deformable sensor holder.

FIG. 8 shows a third embodiment of a deformable sensor holder 200 in accordance with the present invention. In this embodiment, the sensor holder 200 contains first and second members 210, 220 that are substantially rigid in comparison with a deformable interconnecting member 230. As will be appreciated, in this embodiment, all deformation of the sensor holder 200 is isolated in the interconnecting member 230. This allows the first and second members to be pre-formed to interface with a particular patient appendage. As shown, the first and second members 210, 220 are formed to matingly receive a finger and in this regard each contain a finger trough 240. As will be appreciated, utilizing the finger troughs 240, the sensor holder 200 is able to better conform to a patient finger and to provide added light blocking characteristics for a sensor that may be inserted within the troughs 240.

The foregoing description of the present invention has been presented for purposes of illustration and description. Furthermore, the description is not intended to limit the invention to the form disclosed herein. Consequently, variations, adaptations, modifications, and skill and knowledge of the relevant art, are within the scope of the present invention as determined by the claims that follow.

What is claimed is:

1. A medical sensor holder for positioning a medical sensor relative to a patient appendage, comprising:
    an appendage engaging member to which a medical sensor may be selectively connected, said member being plastically deformable to a first shape, wherein said member is also elastically deformable from said first shape to a second shape, and wherein said elastic deformation between said first shape and said second shape provides a resilient retaining force for selective use in attaching said member to an appendage.

2. The medical sensor holder of claim 1, wherein first and second portions of said engaging member are disposable in an opposing relationship when said engaging member is plastically deformed to said first shape.

3. The medical sensor holder of claim 2, wherein said first and second portions of said engaging member are disposable in a spaced opposing relationship.

4. The medical sensor holder of claim 2, wherein at least one of said first and second portions is resiliently deflected relative to the other of said first and second portions when said engaging member is elastically deformed to said second shape.

5. The medical sensor holder of claim 4, wherein said resilient relative deflection creates a compressive force between said opposing first and second portions in said second shape.

6. The medical sensor holder of claim 1, wherein said engaging member further comprises:
    a patient interface layer comprising a compressible material.

7. The medical sensor holder of claim 6, wherein said patient interface layer further comprises:
    an adhesive material.

8. A method for positioning a medical sensor relative to a patient appendage, said method comprising the steps:
    interconnecting a medical sensor to an appendage engaging member;
    plastically deforming said appendage engaging member to a first shape, wherein first and second portions of said engaging member are disposed in a spaced opposing relationship;
    elastically deforming said appendage engaging member from said first shape to a second shape, wherein said first and second portions are elastically deflected relative to one another causing a resilient restoring force therebetween;
    inserting a patient appendage between said first and second portions while said engaging member is in said second shape; and
    utilizing said resilient restoring force to apply a compressive force to said appendage.

9. The method of claim 8, wherein said step of plastically deforming said engaging member comprises bending said engaging member into a U-shaped member wherein said first and second portions are spaced.

10. The method of claim 9, wherein said step of elastically deforming said engaging member comprises applying an outward force between said spaced first and second members.

11. The method of claim 10, wherein said step of utilizing comprises releasing said outward force after said step of inserting.

12. A sensor holder for positioning a sensor relative to a patient appendage, comprising:
    a deformable backing layer, said backing layer being plastically deformable from a first configuration to a second configuration and elastically deformable from said second configuration to a third configuration;
    a patient interface layer having a first surface interconnected to said backing layer and a second inside surface for interfacing with a patient appendage; and
    a sensor recess located on said inside surface for selectively receiving a sensor.

13. A sensor holder as claimed in claim 12, further comprising:
    an adhesive material on said patient interface layer.

14. A sensor holder as claimed in claim 12, wherein in said second configuration, a first portion and a second portion of said sensor holder are disposed in an opposing relationship.

15. A sensor holder as claimed in claim 14, wherein said sensor holder generally comprises a U-shape when said first and second portions are in said opposing relationship.

16. A sensor holder as claimed in claim 14, wherein in said third configuration said first and second portions of said sensor holder are elastically deformed relative to one another.

17. The sensor holder as claimed in claim 14, wherein first and second sections of said sensor recess are located on said first and second portions of said sensor holder.

18. The sensor holder as claimed in claim 12, wherein said recess is configured to:
    matingly receive a correspondingly-shaped sensor.

19. The sensor holder as claimed in claim 12, wherein said recess has a depth formed into said patient interface layer to allow said inside surface of said patient interface layer and a top surface of a sensor to be substantially planer upon application of said sensor to said sensor recess.

20. The sensor holder as claimed in claim 12, wherein said recess further comprises a retainer for selectively attaching a sensor to said sensor holder.

21. The sensor holder as claimed in claim 20, wherein said retainer comprises an adhesive coating on the bottom of said recess.

22. The sensor holder as claimed in claim 21, wherein said adhesive coating is covered with a removable release sheet that may be selectively removed prior to receiving a sensor.

23. The sensor holder as claimed in claim 12, wherein at least one of said deformable backing layer and said patient interface layer is opaque.

24. The sensor holder as claimed in claim 12, wherein said patient interface layer is a compressible material.

25. A method for positioning a sensor relative to a patient appendage, said method comprising the steps:
    providing a deformable sensor holder having at least one sensor recess on an inside patient interface surface;
    locating a sensor in said recess;
    applying a first force to plastically deform said sensor holder wherein a first portion of said sensor holder is disposed in an opposing relationship with a second portion of said sensor holder;

applying second force to etastically deform said first and second portions of said sensor holder outward relative to one another;

locating an appendage between said first and second portions of said sensor holder; and releasing said second force wherein a resilient restoring force of said elastically deformed ortions retains said sensor holder relative to the appendage.

26. The method of claim 25, wherein said locating step further comprises:

seating the sensor in first and second portions of the sensor recess, wherein said first and second sensor portions are disposed in opposing relationship upon application of said sensor holder to said appendage.

27. The method of claim 26, wherein said step of locating a patient appendage further comprises locating said patient appendage over a first portion of said sensor recess on said first portion of said sensor holder.

28. The method of claim 27, wherein said applying a first force further comprises:

disposing said second portion of said sensor recess on an opposing surface of said patient appendage, wherein a line of sight through said appendage is created between said first and second sensor recesses.

29. A medical sensor holder for holding a medical sensor relative to a patient appendage, comprising:

a first member for engaging a first surface of a patient appendage;

a second member for engaging a second surface of a patient appendage; and a plastically deformable interconnecting member having a first end fixedly connected to said first member and a second end fixedly connected to said second member, wherein said interconnecting member interconnects said first member to said second member, said interconnecting member being plastically deformable to a first shape to allow selective positioning of said first member relative to said second member and said interconnecting member is elastically deformable from said first shape to a second shape to provide a resilient for retaining said sensor holder relative to a patient appendage, wherein at least one of said first and second members being interconnectable to a medical sensor.

30. The sensor holder as claimed in claim 29, wherein said plastically deformable interconnecting member allows said first and second members to be disposed to engage substantially opposing surfaces of a patient appendage.

31. The sensor holder as claimed in claim 29, wherein at least one of said first and second members further comprises a compressible material layer for conforming to a surface of a patient appendage.

32. The sensor holder as claimed in claim 29, wherein at least one of said first and second members further comprises a sensor recess that is formed into a patient engaging surface for selectively receiving a medical sensor.

33. The sensor holder as claimed in claim 29, wherein at least one of said first and second members are preformed to conformably engage a patient appendage.

* * * * *

UNITED STATES PATENT AND TRADEMARK OFFICE
CERTIFICATE OF CORRECTION

| | | |
|---|---|---|
| PATENT NO. | : 7,412,272 B2 | Page 1 of 1 |
| APPLICATION NO. | : 11/035083 | |
| DATED | : August 12, 2008 | |
| INVENTOR(S) | : Medina | |

It is certified that error appears in the above-identified patent and that said Letters Patent is hereby corrected as shown below:

Column 13, line 1, delete "etastically", and insert therefor --elastically--.
Column 13, line 7, delete "ortions", and insert therefor --portions--.
Column 14, line 10, after "resilient", insert --force--.

Signed and Sealed this

Seventh Day of October, 2008

JON W. DUDAS
*Director of the United States Patent and Trademark Office*